United States Patent [19]
Bui et al.

[11] Patent Number: 5,632,716
[45] Date of Patent: May 27, 1997

[54] APPARATUS AND METHOD OF MUSCLE TRAINING IN DYNAMIC CARDIOMYOPLASTY

[75] Inventors: Tuan Bui, Highlands Ranch, New Zealand; Gordon Jacobs, Norristown, Pa.; Stuart McConchie, Parker; Thomas Fitzgerald, Morrison, both of Colo.; Valerie Chekanov, Milwaukee, Wis.

[73] Assignee: Telectronics Pacing Systems, Inc., Englewood, Colo.

[21] Appl. No.: 671,779

[22] Filed: Jun. 20, 1996

[51] Int. Cl.⁶ .................................. A61N 1/368
[52] U.S. Cl. ......................................... 600/16
[58] Field of Search ........................ 600/16; 607/5, 607/9, 71, 72

[56] References Cited

U.S. PATENT DOCUMENTS

| | | |
|---|---|---|
| 4,411,268 | 10/1983 | Cox . |
| 4,796,630 | 1/1989 | Regna . |
| 4,813,952 | 3/1989 | Khalafalla ..................... 623/3 |
| 4,869,252 | 9/1989 | Gilli . |
| 5,178,140 | 1/1993 | Ibrahim . |
| 5,215,083 | 6/1993 | Drane et al. . |
| 5,251,621 | 10/1993 | Collins ......................... 607/4 |

Primary Examiner—William E. Kamm
Assistant Examiner—Scott M. Getzow
Attorney, Agent, or Firm—Gottlieb, Rackman & Reisman

[57] ABSTRACT

A pacemaker or similar cardiac and cardiomyoplasty muscle stimulator is provided which during a training period of said muscle, defining alternating training and augmentation phases. During training phases training pulses are provided for the muscle until the muscle is capable of performing cardiac assistance for relatively extended time periods. During the augmentation phases, augmentation pulses are applied to the muscle to provide cardiac assistance even with a muscle with no, or limited training.

7 Claims, 6 Drawing Sheets

APPARATUS AND METHOD OF MUSCLE TRAINING IN DYNAMIC CARDIOMYOPLASTY

BACKGROUND OF THE INVENTION

A. Field of Invention

This invention pertains to an apparatus constructed and arranged to operate in conjunction with a cardiomyoplastic muscle used to assist a heart, and more particularly, to an apparatus arranged and constructed to provide cardiac assist using the cardiomyoplastic muscle immediately after mobilization. Moreover, the apparatus is further used to train the muscle quickly and efficiently.

B. Description of the prior art

Severe chronic cardiac insufficiency arising from cardiac disease or injury shortens and degrades the quality of life of many patients. One form of severe chronic cardiac insufficiency, congestive heart failure, is a pathophysiological state in which cardiac output is inadequate to meet physiological requirements of the body. The mortality rate for congestive heart failure is greater than 50% within five years of onset. Treatments for severe chronic cardiac insufficiency include heart transplants, artificial heart implants and cardiomyoplasty. Cardiac transplantation, using cyclosporine to inhibit tissue rejection, is a very successful technique for prolonging a cardiac patient's life, improving the survival rate to 80% after one year. However, the transplant operation is very expensive and heart availability is limited. The artificial heart approach has had limited success to date.

Dynamic cardiomyoplasty is a surgical and electrical therapeutic technique used to overcome or at least alleviate cardiac insufficiency. This technique consists of using a skeletal muscle which is dissected from a patient, while maintaining its neural tissues and neurovascular structures, and is surgically placed around the patient's heart. An electrical stimulation device, with an electrical pulse generator and intramuscular electrodes, is implanted for performing muscle electrical stimulation in synchrony with ventricular systole to support cardiac pumping.

The skeletal muscles have been considered for use to augment myocardial performance in patients with dilated or ischemic cardiomyopathy. In cardiomyoplasty, the latissimus dorsi muscle (LDM) is wrapped around the heart and stimulated to contract in synchronization with the heart (in systole). In aortomyoplasty, the LDM is wrapped around the aorta and is stimulated to contract in cardiac diastole (counterpulsation). There are also other manifestations of counter pulsation. For example, in skeletal muscle ventricle (SMV), the LDM is wrapped around a small diameter cylinder or cone. The muscle pump is then connected to the circulation in such a way that it may be stimulated to contract during diastole to augment the diastolic blood pressure.

Presently, cardiomyoplasty patients suffering from ventricular fibrillation are treated by one of several methods, depending on the circumstances at the time of the onset of fibrillation. Ventricular fibrillation occurring in the hospital must be first confirmed by doctors or paramedical personnel. Standard high energy defibrillation shocks are then applied to the patient. Of course, these shocks must be applied by people having special training. If the ventricular fibrillation occurs outside a hospital, the patient must wait for trained medical help to arrive and apply the high energy shocks as discussed above.

Commonly assigned U.S. Pat. No. 5,251,621, incorporated herein by reference, proposes a therapy for preventing and terminating cardiac arrhythmias which may lead to ventricular fibrillation and sudden death in patients suffering from congestive heart failure. The proposed therapy combines antiarrhythmic pacing of various forms with skeletal muscle stimulation. Muscle stimulation increases cardiac output, aortic pressure and, therefore, perfusion of the heart to alleviate myocardial ischemia and ameliorate arrhythmias. A device performing pacing, defibrillation and skeletal muscle stimulation is disclosed in U.S. Pat. No. 5,251,621. However, this patent only teaches the stimulation of the skeletal muscle in synchronism with arrhythmia pacing in order to increase cardiac output.

Commonly assigned U.S. Pat. Nos. 4,796,630; 5,178,140; and 5,215,083 disclose devices performing both pacing and defibrillating functions. None of these references disclose, or even suggest, a device capable of performing defibrillation therapy which includes the stimulation of the skeletal muscle as part of the therapy.

In all applications, the stimulation is achieved by electrical pulses applied to the muscle via a pair of intramuscular leads, or a nerve electrode connected to a stimulator.

The latissimus dorsi, being skeletal muscle, is quickly fatigued under normal circumstances. However, repeated stimulation of the skeletal muscle transforms it into a fatigue-resistant muscle suitable for chronic ventricular assistance, enabling dynamic cardiomyoplasty. More specifically, sequential and progressive electrical stimulation of the muscle causes the glycolytic muscle fibers predominant in skeletal muscle to take the form of oxidative fibers. Oxidative fibers are resistant to fatigue and have histochemical and biochemical characteristics similar to the myocardium. The skeletal muscle thus treated is then trained to function so as to assist cardiac muscle to increase the patient's cardiac output.

In a standard application, the muscle tends to be ischemic after mobilization. As a result, electrical stimulation is usually not applied in the first two weeks after mobilization to prevent muscle necrosis. Furthermore, it was found that the original skeletal muscle is prone to fatigue, therefore for the muscle to work continuously, the muscle must be trained and transformed into fatigue resistant. The skeletal muscle can be transformed by low frequency electrical stimulation over a period of about 8 weeks with increasing regularity.

Therefore for about ten weeks after the procedure, the patients will not receive any significant hemodynamic benefits. Coupled with the fact that the patients' condition deteriorate because of the severity of the procedure, this may partially account for the perioperative mortality associated with cardiomyoplasty.

OBJECTIVES AND SUMMARY OF THE INVENTION

In view of the above-mentioned disadvantages of the prior art, it is an objective of the present invention to provide an apparatus which makes use of a skeletal muscle almost immediately after surgery, when the patient needs it the most.

A further objective is to provide an apparatus which trains the muscle automatically thereby eliminating or at least reducing the number of office visits by the patient during the training period.

Yet a further objective is to provide an improved apparatus for training of a skeletal muscle without extensive changes in existing devices.

Other objectives and advantages of the invention shall become apparent from the following description.

It is known that the untrained muscle can contract with full force for a period of time (about 10–20 minutes) before becoming fatigued. Our preliminary study indicates that fatigued muscle can recover most of its strength after a short recovery period. This phenomenon is seen in all human physical activities. For example, a 100 meter runner can run his race at his maximum speed, but can not maintain that speed for 400 meters. However, if allowed to rest after each 100 m stretch, he can run four segments of 100 m at near his maximum speed.

Our invention is based on similar principle. During the training period, we intersperse a number of augmentation periods. In each augmentation period, the muscle is stimulated to obtain maximum muscle contraction for a short period of time (work period) and then allowed to rest (rest period). By having the muscle to contract at maximum, augmentation of cardiac output can be obtained.

There are a number of Work-Rest periods in an augmentation period. After the augmentation period, the muscle is then allowed to continue with its normal training regime. The regime is called Augmentation-Training (AT) regime. The frequency of the augmentation period is increased gradually during the training period.

Furthermore, our invention also allows the augmentation and the training regimes to be changed automatically according to a programmed sequence. This will minimize the inconvenience of having the patients returned to the physician's office during the training period.

Briefly, in accordance with the principles of the present invention, a pacemaker system is provided for stimulating a patient's heart. The patient is also provided with a skeletal muscle grafted onto the heart to assist its cardiac functions. The pacemaker system includes means for analyzing signals from the heart for detecting, classifying and correcting abnormal episodes or conditions of the heart such as arrhythmia. The pacemaker system further includes heart stimulating means for generating and delivering stimulating pulses of various amplitudes to the heart. These stimulating means may include pacing electrodes, as well as defibrillating electrodes, receiving the various pulses. These pulses may be characteristic of standard pacemaker stimulation, cardioversion or defibrillation shocks. The pacemaker system also includes at least one muscle stimulation electrode which is adapted to be placed in electrical contact with the muscle graft. This electrode receives muscle stimulating pulses from a muscle pulse stimulating means.

During a training period, the muscle is trained to convert it from a muscle capable doing work only intermittently to a muscle capable of performing work substantially continuously. At the beginning of his period, i.e., during implantation of the muscle, a clinician sets up a training schedule. This schedule specifies several sequential training phases. In each phase, the muscle being stimulated so that it is performing more and more work. Importantly, each training phase is interrupted at predetermined augmentation intervals. During these intervals, the muscle is stimulated to perform work at short periods separated by rests.

DETAILED DESCRIPTION OF THE INVENTION

This invention relates to a novel myostimulator to stimulate the muscle during the training period. The method allows the muscle to be trained, but also provide significant hemodynamic benefit to the patients without causing the muscle to be overtly fatigue leading to potential necrosis.

Figure 5:
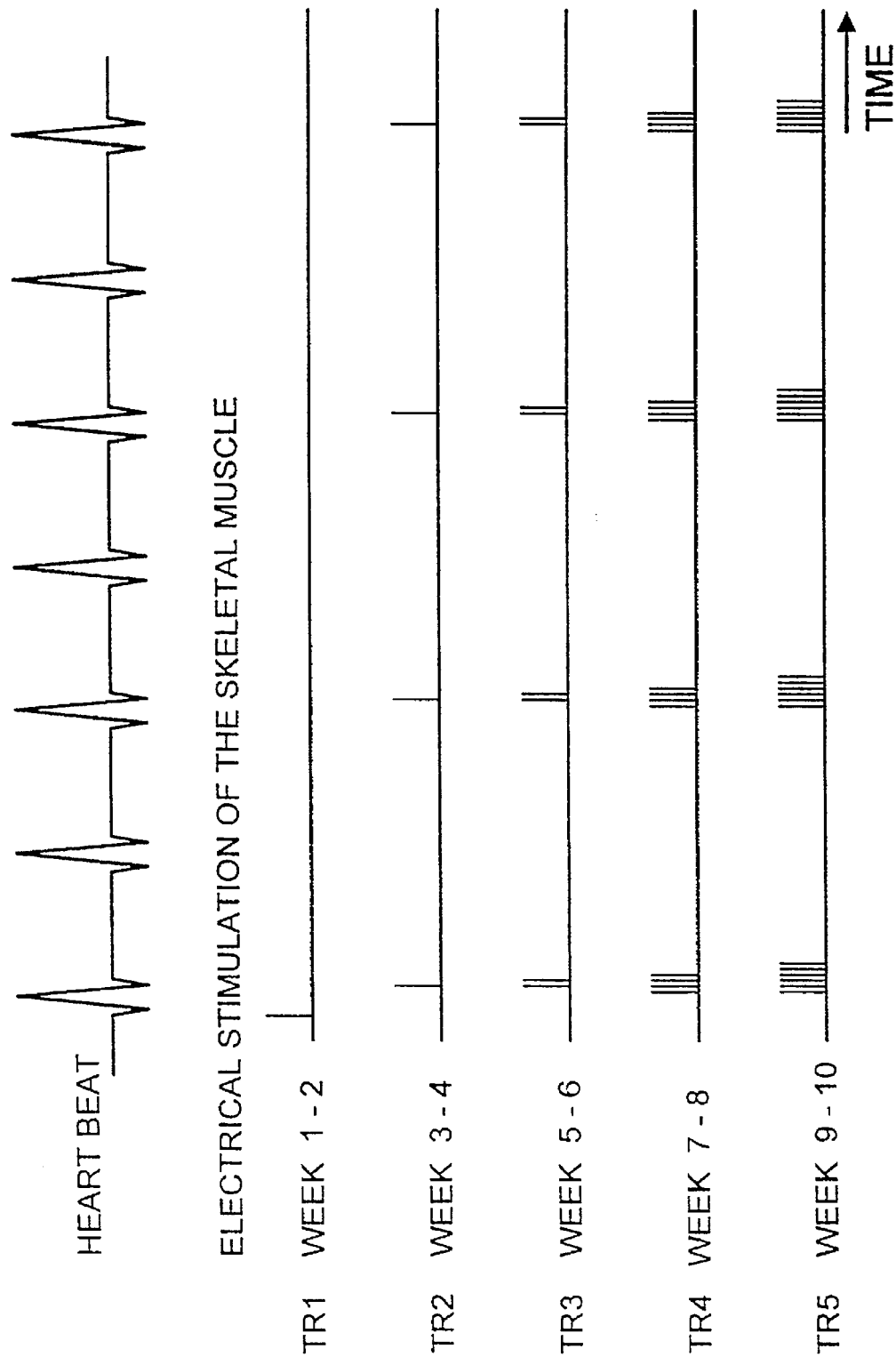
FIG. 5 shows a prior art training period controlled by the physician.

FIG. 5 shows a typical training regime used in cardiomyoplasty in a ten week period. No electrical stimulation is applied in the first two weeks after the operation. At the end of the two week period, the patient is asked to return to the physician's office. The myostimulator is then programmed to change to one electrical pulse every second heart beat (weeks third & fourth). At the end of the fourth week, the patient is asked to return to the physician's office again. The stimulation is increased to a burst of two pulses, again at every second heart beat (fifth and sixth week). The burst is increased to four pulses for two weeks and then six pulses. At that time the muscle is considered trained and fully transformed. During chronic stimulation of the muscle, usually a burst of six pulses is used. Thus the patient is required to return to the physician's office for reprogramming of the training regime every two weeks during the training period.

Prior art slowly increases the muscle stimulation during the first eight to ten weeks after the operation with the sole aim of conditioning and transforming the skeletal muscle into fatigue resistant muscle type. Therefore, during this period, no significant hemodynamic benefit is available to the patient. Because the patient has congestive heart disease, this is a crucial period for the patient to receive cardiac assistance, especially after an open heart surgery, which significantly deteriorates the patient's condition.

Furthermore, the patient is required to return to the physician's office every two weeks during the training period for reprogramming of the stimulation burst. This is highly inconvenient for the patient, who may not be in the best of health at that stage.

Figure 1:
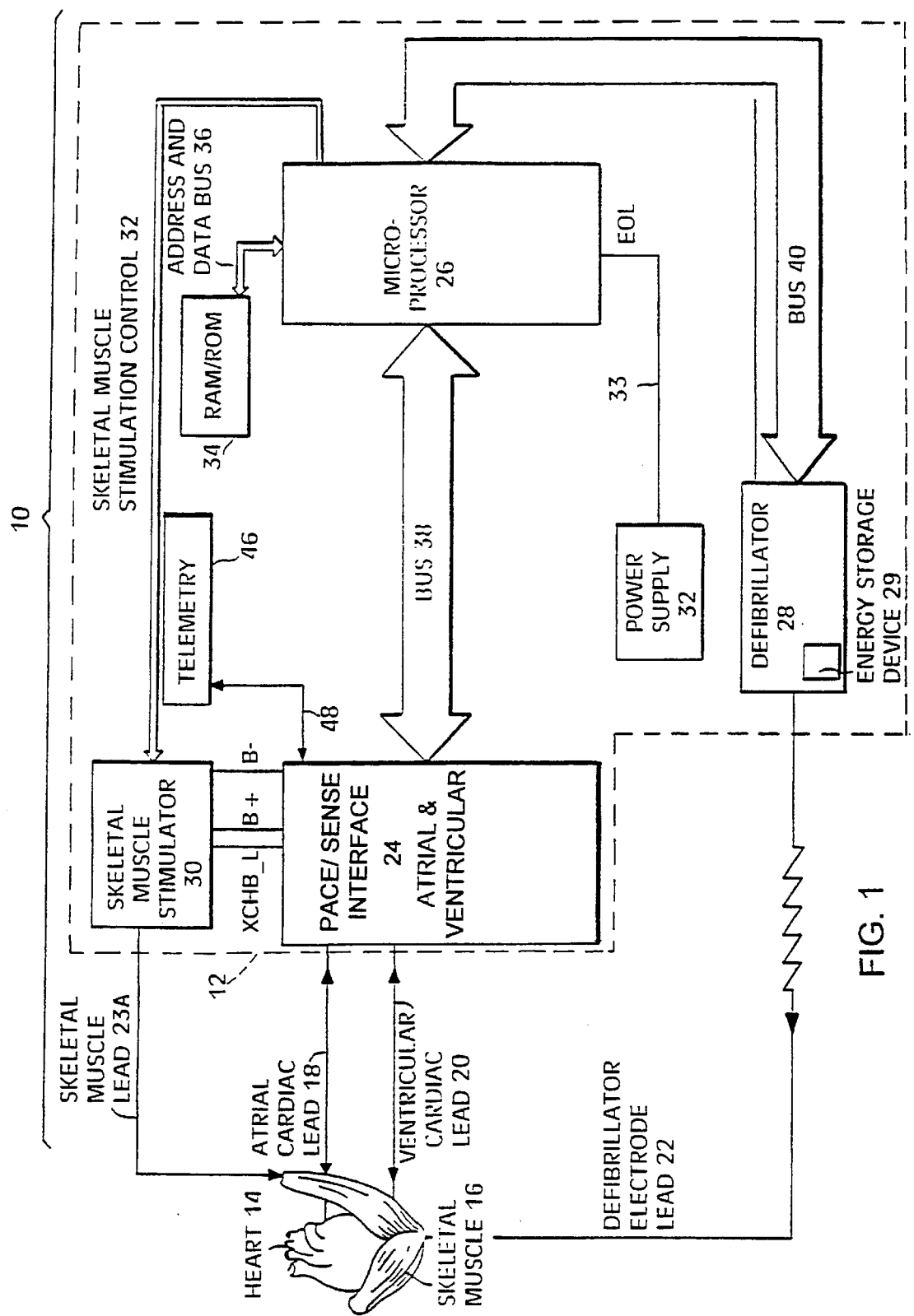
FIG. 1 is a block diagram of an implanted pacemaker system constructed in accordance with this invention, including a rate-responsive, dual chamber arrhythmia control system.

In FIG. 1 there is depicted a block diagram of a pacemaker system 10. The system 10 is designed to be implanted within a patient and includes a pulse generator module or pacemaker 12 and leads for connecting module 10 to a patient's heart 14 and skeletal muscle 16. These leads include an atrial cardiac lead 18, a ventricular cardiac lead 20 extending to the atrium and the ventricle of the patient's heart 14, respectively, as well as a defibrillation electrode lead 22 and a skeletal muscle lead 23.

The pacemaker 12 generally includes an interface 24, a microprocessor 26, a defibrillator 28, a skeletal muscle simulator 30 and a power supply 32. The interface 24 is provided for the detection of analog signals representing cardiac electrical activity and for the delivery of pacing pulses to the heart over leads 18 and 20. The microprocessor 26, in response to various inputs received from the interface 24 as well as from a defibrillator 16, performs various operations so as to generate different control and data outputs to pacemaker interface 24, skeletal muscle stimulator 30 and defibrillator 28. The power supply 32 provides reliable voltage to the other components of the pulse module. When the power supply 32 is nearly exhausted it generates an End-Of-Life (EOL) signal on line 33 to the microprocessor 26.

Skeletal muscle stimulator 30 generates electrical pulses on skeletal muscle lead 23 for stimulating the skeletal muscle 16. The pulses to muscle 16 are generated according to timed control signals from microprocessor 26 received via skeletal muscle stimulation control bus 32.

The defibrillator 28 has an energy storage device 29 which may consist of one or more capacitors (not shown), and is used to produce high voltage defibrillation shocks responsive to control signals from microprocessor 26 received on bus 40. The defibrillator electrode lead 22 transmits the defibrillation shocks from the implanted pacemaker 12 to the heart 14.

The microprocessor 26 is connected to a Random Access/Read Only memory unit 34 by an address and data bus 36.

The pacemaker 12 also includes a telemetry circuit 46 over which control signals and cardiac signals can be exchanged with the outside world. The telemetry circuit 46 is coupled to interface 24 by a bus 48.

Microprocessor 26 and interface 24 are connected by a data and communication bus 38 for exchanging various data.

Figure 2:
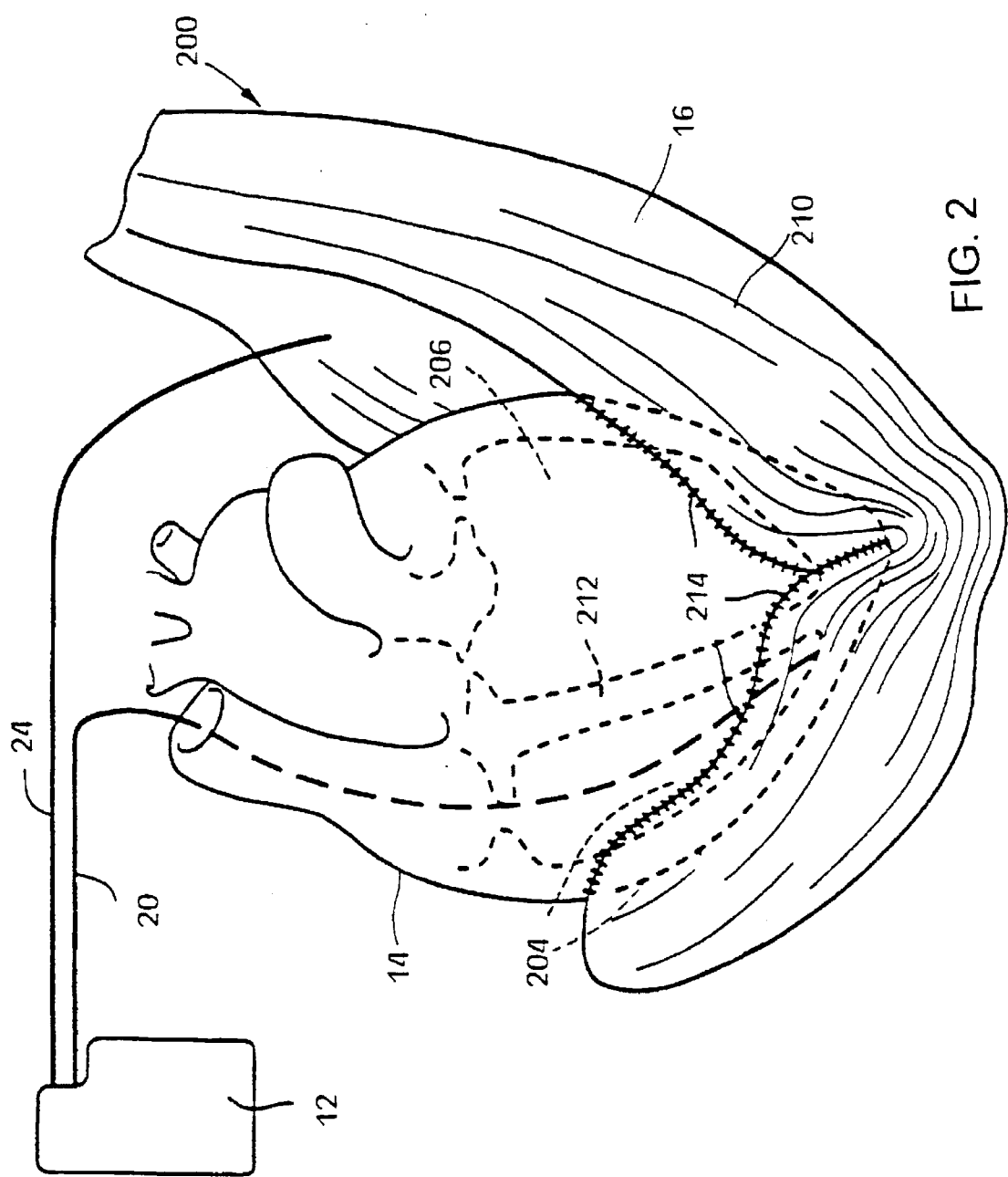
FIG. 2 shows a somewhat simplified side elevational view of a skeletal muscle and provided with the system of FIG. 1.

FIG. 2 illustrates an example of a cardiac assist arrangement 200 for performing cardiac pacing, long-term stimulation of skeletal muscles using systolic augmentation, and defibrillation of the heart. A latissimus dorsi skeletal muscle 16 is positioned over the right ventricle 204 and left ventricle 206 of a patient's heart 14. The longitudinal fibers 210 of the latissimus dorsi are oriented generally parallel to the longitudinal axes of the ventricles 204 and 206 and interventricular septum 212 of the heart. The skeletal muscle 16 is positioned in this manner so that when it is stimulated, it compresses the ventricles, particularly the left ventricle 206, and augments the force of right and left ventricular contractions.

The ventricular cardiac lead 20 is implanted in or on the heart's right ventricle 204 and the skeletal muscle lead 24 extends from the muscle stimulator 30 (shown in FIG. 1) to the muscle 16. The skeletal muscle lead 24 may be placed directly on a nerve or placed near nerve branches within the muscle 16 to provide for selective depolarization of intact motor nerve fibers. In this manner the muscle 16 is forced selectively to contract about the heart 14, for either systolic augmentation or defibrillation.

Details of the interface 24 and its method of operation are found in U.S. Pat. No. 5,251,621 discussed above and incorporated herein by reference.

Figure 3:
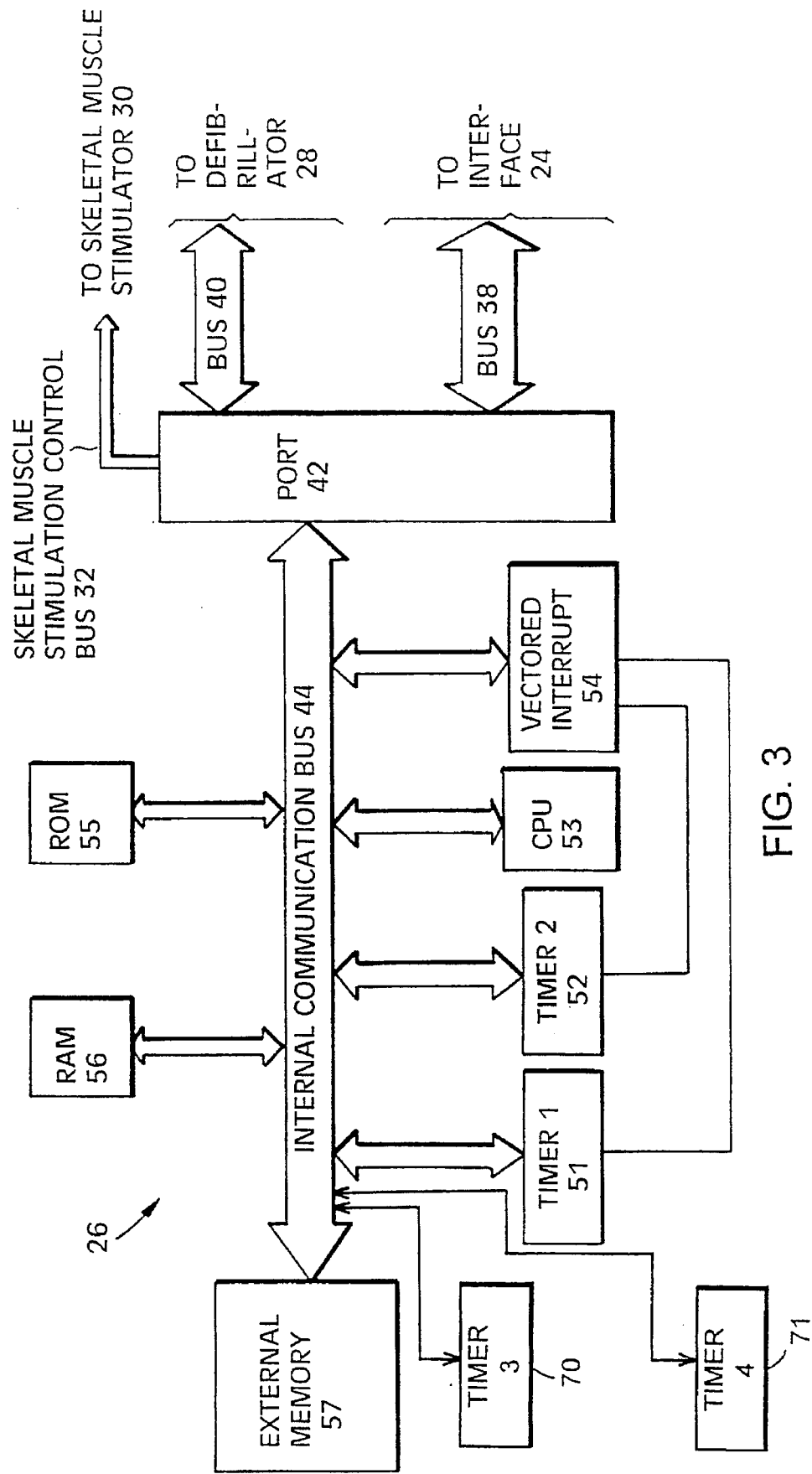
FIG. 3 shows a block diagram of the microprocessor of the pacemaker system of FIG. 3.

Referring to FIG. 3, microprocessor 26 comprises two timers 51 and 52, a CPU 53, a vectored interrupts block 54, a ROM 55, a RAM 56, an external memory 57, a port 42 and an internal communications bus 44. RAM 56 acts as a scratch pad and active memory during execution of the various programs stored in ROM 55 and used by microprocessor 26. These programs include system supervisory programs, detection algorithms for detecting and confirming various arrhythmias, and programming for implementing the flow chart of FIG. 4 as well as storage programs for storing, in external memory 57, data concerning the functioning of module 12 and electrograms provided by atrial and/or ventricular cardiac lead(s) 20 (FIG. 1). Timers 51 and 52, and associated control software, implement standard timing functions required by microprocessor 26.

Microprocessor 26 receives various status and control inputs from the interface 24 and defibrillator 16 on buses 38 and 40 and produces the control signals on these buses and bus 32 necessary for various functions including normal rate responsive pacing of the atria and/or ventricle, skeletal muscle stimulation and defibrillation.

More specifically, the atrial and ventricular pace control inputs derived from the signals received from the heart on leads 18 and 20 determine the respective types of atrial and/or ventricular pacing to be delivered to the heart. Details of this function are described in commonly assigned U.S. Pat. No. 4,869,252 to Norma Louise Gilli, issued Sep. 26, 1989, entitled "Apparatus And Method For Controlling Pulse Energy In Antitachyarrhythmia And Bradycardia Pacing Devices," and incorporated herein by reference.

The skeletal muscle stimulator 30 shown in FIG. 1, receives input signals from microprocessor 26 over the skeletal muscle stimulation control bus 32. In addition, the interface 24 supplies to stimulator 30 battery power over two battery leads B+ and B− which provide energy for biphasic skeletal muscle stimulation. The battery leads B+, B− are floating with respect to the power supplied by supply 32 to provide signal isolation. The signal XCHB_L is a cross channel blanking control signal used to disable cardiac sensing by the interface 24 during generation of a skeletal muscle stimulation pulse. Therefore this signal prevents the microprocessor 26 from incorrectly classifying a skeletal muscle stimulation pulse as an episode of intrinsic cardiac activity. Details of the skeletal muscle stimulator are provided in commonly assigned U.S. Pat. No. 5,251,621, incorporated herein by reference.

In addition, the controller 26 further includes additional timers 3 and 4 designated in FIG. 3 by numerals 70 and 71 respectively. These timers are used to designate various phases during the training periods. Except for the training sequence described below, the operation of the device has been described, for example, in U.S. Pat. No. 5,251,621.

Figure 4:
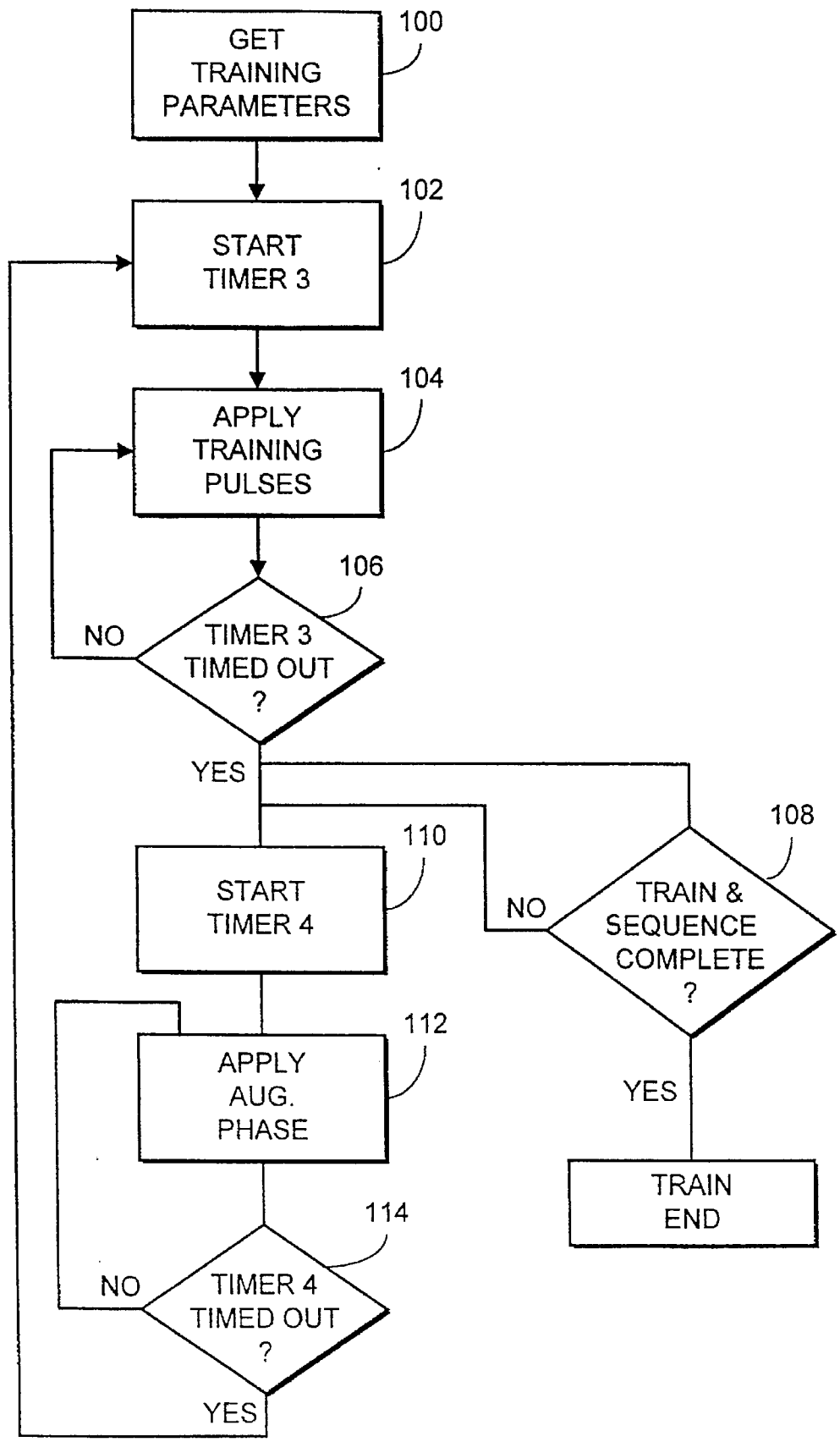
FIG. 4 shows a flow chart for the operation of the pacemaker system of FIG. 1.
Figure 6:
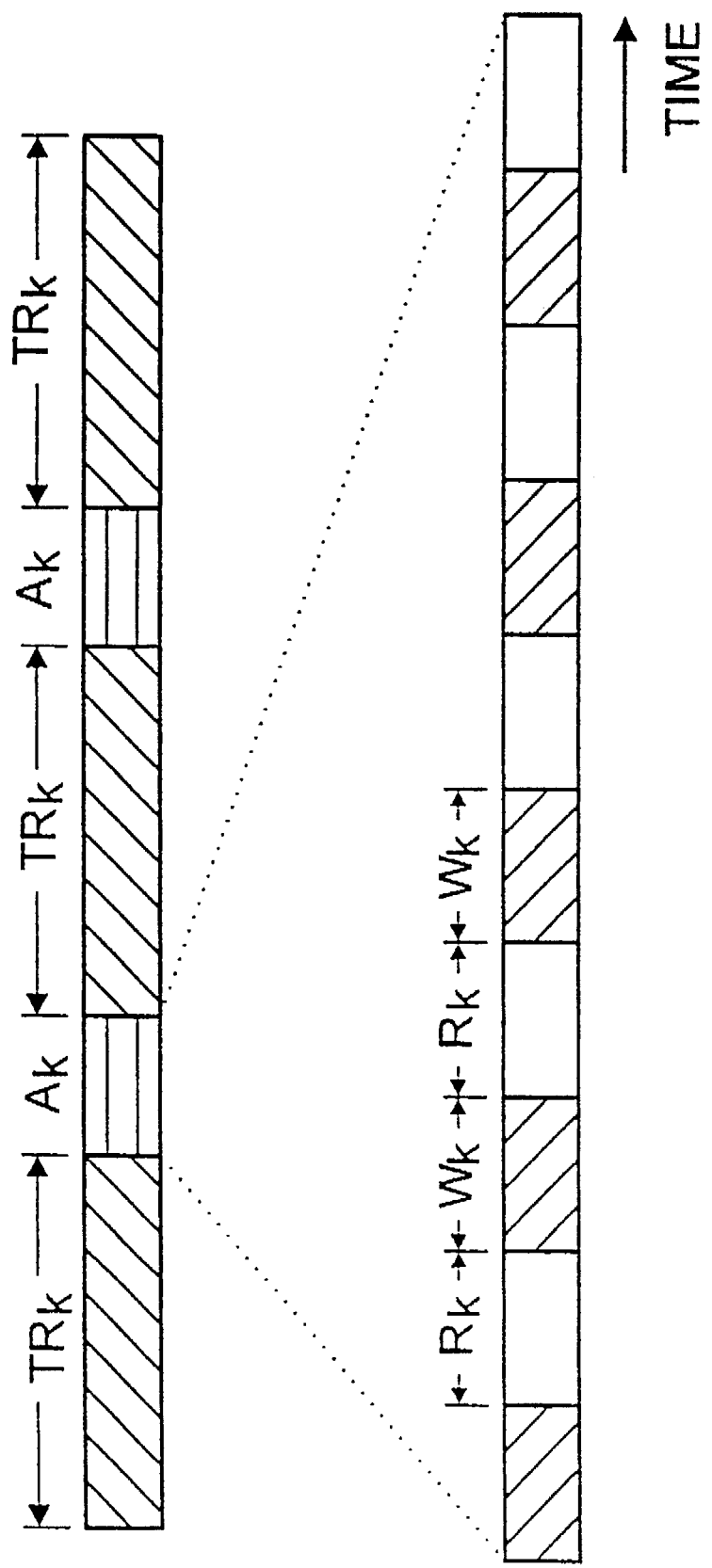
FIG. 6 shows a training period consisting of sequential training phases interrupted by augmentation periods, in accordance with the present invention.

The operation of the pacemaker system 10 is now described in conjunction with the flow chart of FIG. 4 and the timing diagrams of FIGS. 5 and 6. The training sequence consists of several training periods, each consisting of training phases interspersed with augmentation phases. After implantation, in step 100, the pacemaker 12 receives from the clinician, through a programmer (not shown) the desired training parameters. During the augmentation phases, the muscle 16 is stimulated at an increased rate and amplitude than is normally associated with training. The augmentation phases consist of successive work and rest cycles.

The training parameters include the number of training periods, the length of each training period, the stimulation characteristics (i.e. frequency and, optionally, amplitude of each stimulation) and so on. In addition, the parameters also define the characteristics of the training and augmentation phases, including the frequency of augmentation phases, the duration of the augmentation phases, the lengths of the work and rest cycles, the characteristics of the stimulations during the work cycles, and so on.

In step 102, the training sequence is initiated by starting timer 3. The training sequence is composed of k training periods lasting, for example, 1–2 weeks each. As shown in FIG. 6, each training period consists of a training phase TRk followed by an augmentation phase Ak. The duration of the training sequence, the number of training periods k, the duration of the training and augmentation phases Trk, Ak are all programmable parameters set during step 100. During the training phases Trk several pulses are applied to the muscle. Each augmentation phase consists sequentially of work sections Wk followed by rest sessions Rk, as seen in FIG. 5.

During the rest sessions, no pulses are applied to the muscle. During the work sessions Wk, one or more pulses are applied to the muscle. The duration of the work and rest sessions Wk, Rk and the number of pulses in each work session Wk are also parameters set during step 100.

During the training phase Trk pulses are applied to the muscle as shown in FIG. 6. Preferably during the first training phase TR1, no pulses are applied, and then in each subsequent session more and more pulses are applied. Similarly, initially, the number and frequency of pulses applied during the work session W1 is preferably low. For example, a pulse may be applied coincident with every tenth heart beat. Thereafter the frequency and number of pulses may be increased. Typical values for the durations of Trk, Ak, Wk, Rk for k>1 may be:

Trk=120 min

Ak=40 min

Wk=2 min

Rk=2 min

Referring back to FIG. 4, in step timer 3 is started. Timer 3 times out at the end of the duration of Trk. In step 104, pulses are applied to the muscle (if any) as illustrated in FIG. 6. When the timer 3 times out (step 106) a test is performed (step 108) to check if the whole training sequence is complete. If it is not than in step 110 timer 4 is started. Timer 4 is used to indicated the duration of the augmentation periods Ak. During this time, the muscle is alternately pulsed and rested (step 112) as shown in FIG. 6. When the timer 4 times out (step 114), timer 3 is initiated again (step 102).

Preferably during programming, the programmer may be configured to calculated and display the percentage of work time per day (or other criteria) as the clinician is making his selection to further assist the clinician in his parameter choices.

The invention described here has two major advantages. First, it provides for cardiac assistance to the patient during the critical recovery period. Second, it obviates the need for frequent travel by the patient to the clinician, especially early in the recovery period when the patient may not be fit, or may have difficulty traveling.

Although the invention has been described with reference to a particular embodiment, it is to be understood that this embodiment is merely illustrative of the application of the principles of the invention and that the same objectives may be accomplished by other means as well. For example, instead of a muscle, another biocompatible mechanical member may be wrapped about the heart, which member may be selectively contracted and extended as required to eject blood from the heart prior to defibrillation therapy. Accordingly, the embodiment described in particular should be considered exemplary, not limiting, with respect to the following claims.

We claim:

1. An cardiomyoplasty control device for controlling an implanted muscle arranged and constructed to provide cardiac assistance, said control device comprising:

electrode means for delivering stimulation pulses to said muscle; and timing means for controlling the timing of said stimulation pulses, said timing means defining a sequence of training periods, each training period including augmentation phases interlaced with training phases, wherein in said training phases said stimulation pulses are applied at a first interval selected to train said muscle; and wherein in said augmentation periods, said stimulation pulses are applied at a second interval selected to augment the cardiac function.

2. The control device of claim 1 wherein said sequence includes an initial training period during which no stimulation pulses are applied.

3. The control device of claim 1 wherein said first and second intervals are gradually decreased from one training or augmentation phase to a next training or augmentation phase.

4. An implantable pacemaker for providing pulses to a patient's heart and to a muscle arranged to assist said heart, said pacemaker comprising:

cardiac pulsing means for generating cardiac pulses for said heart;

muscle pulsing means for generating muscle pulses for said muscle; and control means for controlling said cardiac and muscle pulsing means, said control means including timing means for defining a sequence of training periods consisting of training phases during which training pulses are selectively generated to train said muscle, and augmentation phases interspace with said training phases, wherein during said augmentation phases augmentation pulses are generated for said muscle for augmenting the cardiac function.

5. The pacemaker of claim 4 wherein said control mean includes a timer for defining a plurality of work sessions alternating with rest sessions, said work and rest sessions defining said augmentation periods.

6. The pacemaker of claim 5 further comprising input means for receiving training parameters from an operator, said training parameters defining said training and augmentation periods.

7. The pacemaker of claim 4 wherein in successive augmentation phases at least one of a augmentation amplitude of said augmentation pulses, and augmentation interval between said pulses is changed.

* * * * *